US009867657B2

(12) United States Patent
Twomey

(10) Patent No.: US 9,867,657 B2
(45) Date of Patent: *Jan. 16, 2018

(54) SURGICAL FORCEPS

(71) Applicant: COVIDIEN LP, Mansfield, MA (US)

(72) Inventor: John R. Twomey, Superior, CO (US)

(73) Assignee: COVIDIEN LP, Mansfield, MA (US)

( * ) Notice: Subject to any disclaimer, the term of this patent is extended or adjusted under 35 U.S.C. 154(b) by 428 days.

This patent is subject to a terminal disclaimer.

(21) Appl. No.: 14/597,433

(22) Filed: Jan. 15, 2015

(65) Prior Publication Data
US 2015/0127000 A1 May 7, 2015

Related U.S. Application Data

(63) Continuation of application No. 13/102,573, filed on May 6, 2011, now Pat. No. 8,939,972.

(51) Int. Cl.
A61B 18/12 (2006.01)
A61B 18/14 (2006.01)
(Continued)

(52) U.S. Cl.
CPC .......... *A61B 18/1445* (2013.01); *A61B 17/12* (2013.01); *A61B 2017/320052* (2013.01);
(Continued)

(58) Field of Classification Search
CPC ................ A61B 17/12; A61B 18/1445; A61B 2017/320052; A61B 2018/00297;
(Continued)

(56) References Cited

U.S. PATENT DOCUMENTS

D249,549 S 9/1978 Pike
D263,020 S 2/1982 Rau, III
(Continued)

FOREIGN PATENT DOCUMENTS

CN 201299462 9/2009
DE 2415263 A1 10/1975
(Continued)

OTHER PUBLICATIONS

Int'l Search Report EP 07 015191.5 dated Jan. 23, 2008.
(Continued)

*Primary Examiner* — Daniel Fowler

(57) ABSTRACT

A forceps includes an end effector assembly having first and second jaw members disposed in opposed relation relative to one another. One (or both) of the jaw members is moveable with respect to the other from a spaced-apart position to an approximated position for grasping tissue therebetween. A knife is longitudinally translatable with respect to the first and second jaw members between a retracted position, an intermediate position, and an extended position. The knife coupled to one or both of the jaw members via a pin-slot engagement such that, upon translation of the knife from the retracted position to the intermediate position, the first and second jaw members are moved to the approximated position to grasp tissue therebetween and such that, upon translation of the knife from the intermediate position to the extended position, the knife is extended between the jaw members to cut tissue grasped therebetween.

5 Claims, 9 Drawing Sheets

(51) Int. Cl.
    *A61B 17/12*     (2006.01)
    *A61B 17/32*     (2006.01)
    *A61B 18/00*     (2006.01)
    *A61B 90/00*     (2016.01)

(52) U.S. Cl.
    CPC ............... *A61B 2018/00297* (2013.01); *A61B 2018/00642* (2013.01); *A61B 2018/1455* (2013.01); *A61B 2090/0811* (2016.02)

(58) Field of Classification Search
    CPC .. A61B 2018/00642; A61B 2018/1455; A61B 2090/0811
    See application file for complete search history.

(56) References Cited

U.S. PATENT DOCUMENTS

| | | | |
|---|---|---|---|
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| D384,413 S | 9/1997 | Zlock et al. |
| H1745 H | 4/1998 | Paraschac |
| D402,028 S | 12/1998 | Grimm et al. |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| H1904 H | 10/2000 | Yates et al. |
| 6,245,085 B1 | 6/2001 | Benecke et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| 7,011,657 B2 | 3/2006 | Truckai et al. |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| 7,628,791 B2 | 12/2009 | Garrison et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| 8,147,489 B2 | 4/2012 | Moses et al. |
| 8,298,233 B2 | 10/2012 | Mueller |
| 8,394,096 B2 | 3/2013 | Moses et al. |
| 8,409,246 B2 | 4/2013 | Kerr et al. |
| 8,409,247 B2 | 4/2013 | Garrison et al. |
| 8,425,511 B2 | 4/2013 | Olson |
| 8,430,877 B2 | 4/2013 | Kerr et al. |
| 8,439,913 B2 | 5/2013 | Horner et al. |
| 8,469,716 B2 | 6/2013 | Fedotov et al. |
| 8,469,991 B2 | 6/2013 | Kerr |
| 8,469,992 B2 | 6/2013 | Roy et al. |
| 8,480,671 B2 | 7/2013 | Mueller |
| 8,491,624 B2 | 7/2013 | Kerr et al. |
| 8,491,625 B2 | 7/2013 | Horner |
| 8,491,626 B2 | 7/2013 | Roy et al. |
| 8,512,336 B2 | 8/2013 | Couture |
| 8,540,749 B2 | 9/2013 | Garrison et al. |
| 8,551,091 B2 | 10/2013 | Couture et al. |
| 8,556,929 B2 | 10/2013 | Harper et al. |
| 8,568,397 B2 | 10/2013 | Horner et al. |
| 8,568,408 B2 | 10/2013 | Townsend et al. |
| 8,585,736 B2 | 11/2013 | Horner et al. |
| 8,597,295 B2 | 12/2013 | Kerr |
| 8,623,018 B2 | 1/2014 | Horner et al. |
| 8,628,557 B2 | 1/2014 | Collings et al. |
| 8,641,712 B2 | 2/2014 | Couture |
| 8,647,343 B2 | 2/2014 | Chojin et al. |
| 8,652,135 B2 | 2/2014 | Nau, Jr. |
| 8,663,222 B2 | 3/2014 | Anderson et al. |
| 8,672,939 B2 | 3/2014 | Garrison |
| 8,685,009 B2 | 4/2014 | Chernov et al. |
| 8,685,021 B2 | 4/2014 | Chernov et al. |
| 8,702,749 B2 | 4/2014 | Twomey |
| 8,734,445 B2 | 5/2014 | Johnson et al. |
| 8,740,898 B2 | 6/2014 | Chojin et al. |
| 8,745,840 B2 | 6/2014 | Hempstead et al. |
| 8,784,418 B2 | 7/2014 | Romero |
| 8,795,269 B2 | 8/2014 | Garrison |
| 8,808,288 B2 | 8/2014 | Reschke |
| 8,814,864 B2 | 8/2014 | Gilbert |
| 8,840,639 B2 | 9/2014 | Gerhardt, Jr. et al. |
| 8,852,185 B2 | 10/2014 | Twomey |
| 8,858,553 B2 | 10/2014 | Chojin |
| 8,888,775 B2 | 11/2014 | Nau, Jr. et al. |
| 8,900,232 B2 | 12/2014 | Ourada |
| 8,906,018 B2 | 12/2014 | Rooks et al. |
| 8,920,421 B2 | 12/2014 | Rupp |
| 8,932,293 B2 | 1/2015 | Chernov et al. |
| 8,936,614 B2 | 1/2015 | Allen, IV |
| 8,939,972 B2 | 1/2015 | Twomey |
| 8,945,175 B2 | 2/2015 | Twomey |
| 8,961,504 B2 | 2/2015 | Hoarau et al. |
| 8,968,283 B2 | 3/2015 | Kharin |
| 8,968,305 B2 | 3/2015 | Dumbauld et al. |
| 8,968,316 B2 | 3/2015 | Roy et al. |
| 8,968,357 B2 | 3/2015 | Mueller |
| 8,968,359 B2 | 3/2015 | Kerr et al. |
| 9,005,200 B2 | 4/2015 | Roy et al. |
| 9,017,372 B2 | 4/2015 | Artale et al. |
| 2003/0055424 A1* | 3/2003 | Ciarrocca ............ A61B 18/1445 606/51 |
| 2003/0114851 A1 | 6/2003 | Truckai et al. |
| 2003/0199869 A1 | 10/2003 | Johnson et al. |
| 2007/0106295 A1 | 5/2007 | Garrison et al. |
| 2009/0326531 A1 | 12/2009 | Geiselhart |
| 2010/0076433 A1* | 3/2010 | Taylor ................ A61B 18/1445 606/52 |
| 2010/0179545 A1 | 7/2010 | Twomey et al. |
| 2010/0274244 A1 | 10/2010 | Heard |
| 2011/0087221 A1 | 4/2011 | Siebrecht et al. |
| 2011/0193608 A1 | 8/2011 | Krapohl |
| 2011/0270245 A1 | 11/2011 | Horner et al. |
| 2011/0270251 A1 | 11/2011 | Horner et al. |
| 2011/0276049 A1 | 11/2011 | Gerhardt |
| 2011/0295313 A1 | 12/2011 | Kerr |
| 2011/0319888 A1 | 12/2011 | Mueller et al. |
| 2012/0059372 A1 | 3/2012 | Johnson |
| 2012/0059375 A1 | 3/2012 | Couture et al. |

(56) References Cited

U.S. PATENT DOCUMENTS

| | | |
|---|---|---|
| 2012/0059409 A1 | 3/2012 | Reschke et al. |
| 2012/0083786 A1 | 4/2012 | Artale et al. |
| 2012/0123404 A1 | 5/2012 | Craig |
| 2012/0123410 A1 | 5/2012 | Craig |
| 2012/0130367 A1 | 5/2012 | Garrison |
| 2012/0172868 A1 | 7/2012 | Twomey et al. |
| 2012/0239034 A1 | 9/2012 | Horner et al. |
| 2012/0259331 A1 | 10/2012 | Garrison |
| 2012/0265241 A1 | 10/2012 | Hart et al. |
| 2012/0296205 A1 | 11/2012 | Chernov et al. |
| 2012/0296238 A1 | 11/2012 | Chernov et al. |
| 2012/0296239 A1 | 11/2012 | Chernov et al. |
| 2012/0296317 A1 | 11/2012 | Chernov et al. |
| 2012/0296323 A1 | 11/2012 | Chernov et al. |
| 2012/0296324 A1 | 11/2012 | Chernov et al. |
| 2012/0303025 A1 | 11/2012 | Garrison |
| 2012/0323238 A1 | 12/2012 | Tyrrell et al. |
| 2012/0330308 A1 | 12/2012 | Joseph |
| 2012/0330309 A1 | 12/2012 | Joseph |
| 2013/0018364 A1 | 1/2013 | Chernov et al. |
| 2013/0018371 A1 | 1/2013 | Twomey |
| 2013/0018372 A1 | 1/2013 | Sims et al. |
| 2013/0022495 A1 | 1/2013 | Allen, IV et al. |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 10045375 C2 | 10/2002 |
| DE | 20 2007 009317 U1 | 8/2007 |
| DE | 202007009165 U1 | 8/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1 159 926 A2 | 12/2001 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-317934 A | 12/1996 |
| JP | 9-10223 C | 1/1997 |
| JP | 9-122138 A | 5/1997 |
| JP | 10-155798 A | 6/1998 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000342599 A | 12/2000 |
| JP | 2000350732 A | 12/2000 |
| JP | 2001-8944 | 1/2001 |
| JP | 2001-29356 | 2/2001 |
| JP | 2001128990 A | 5/2001 |
| JP | 2001-190564 A | 7/2001 |
| JP | 2004-517668 A | 6/2004 |
| JP | 2004-528869 A | 9/2004 |
| SU | 401367 A1 | 10/1973 |
| WO | 0036986 A1 | 6/2000 |
| WO | 0115614 A1 | 3/2001 |
| WO | 0154604 A1 | 8/2001 |
| WO | 2005/110264 A2 | 11/2005 |

OTHER PUBLICATIONS

Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 185386.9 dated Jan. 10, 2011.
Int'l Search Report EP 10 185405.7 dated Jan. 5, 2011.
Int'l Search Report EP 10 157500.9 dated Jul. 30, 2010.
Int'l Search Report EP 10 159205.3 dated Jul. 7, 2010.
Int'l Search Report EP 10 160870,1 dated Aug. 9, 2010.
Int'l Search Report EP 10 161596.1 dated Jul. 28, 2010.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182022.3 dated Mar. 11, 2011.
Int'l Search Report EP 10 189206.5 dated Mar. 17, 2011.
Int'l Search Report EP 10 191320.0 dated Feb. 15, 2011.
European Office Action corresponding to counterpart Int'l Appln. No. EP 12 16 6780.2, dated Feb. 23, 2016.
European Office Action corresponding to counterpart Int'l Appln. No. EP 12 16 6780.2 dated Nov. 16, 2016.
European Search Report for European Application No. 12166780.2 dated Aug. 16, 2012.
U.S. Appl. No. 08/926,869, filed Sep. 10, 1997, James G. Chandler.
U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremeich.
Michael Choti, "Abdominoperineal Resection with the LigaSure Vessel Sealing System and LigaSure Atlas 20 cm Open Instrument"; Innovations That Work, Jun. 2003.

(56) References Cited

OTHER PUBLICATIONS

Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte,NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12:876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.

Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 161117.4 dated Jun. 30, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.

(56) References Cited

OTHER PUBLICATIONS

Int'l Search Report PCT/US08/61498 dated Sep. 22, 2008.
Int'l Search Report PCT/US09/032690 dated Jun. 16, 2009.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.

* cited by examiner

SURGICAL FORCEPS

This application is a continuation application of U.S. patent application Ser. No. 13/102,573, filed on May 6, 2011, the entire contents of which are hereby incorporated herein by reference.

BACKGROUND

Technical Field

The present disclosure relates to a surgical forceps, and more particularly, to an electrosurgical forceps capable of sealing and cutting tissue.

Background of Related Art

A forceps is a plier-like instrument that relies on mechanical action between its jaws to grasp, clamp and constrict vessels or tissue. Electrosurgical forceps utilize both mechanical clamping action and electrical energy to affect hemostasis by heating tissue and blood vessels to coagulate and/or cauterize tissue. Certain surgical procedures require more than simply cauterizing tissue and rely on the unique combination of clamping pressure, precise electrosurgical energy control and gap distance (i.e., distance between opposing jaw members when closed about tissue) to "seal" tissue, vessels and certain vascular bundles.

Typically, once a vessel is sealed, the surgeon has to accurately sever the vessel along the newly formed tissue seal. Accordingly, many vessel sealing instruments have been designed that incorporate a knife or blade member that effectively severs the tissue after forming a tissue seal. Many of such instruments require the surgeon to actuate a first trigger to grasp tissue between the jaw members, e.g., to perform the sealing operation, and then to actuate a second trigger once the tissue seal has been formed, to advance the knife through tissue to sever the newly formed tissue seal.

It would therefore be advantageous to develop an instrument that reduces the number of steps required to grasp, seal, and cut tissue. For example, commonly-assigned U.S. Pat. No. 7,628,791 to Garrison et al., the entire contents of which are hereby incorporated by reference herein, discloses a single-action tissue sealer capable of grasping, sealing and cutting tissue in a single action.

SUMMARY

In accordance with the present disclosure, a forceps is provided. The forceps includes an end effector assembly having first and second jaw members disposed in opposed relation relative to one another. One (or both) of the jaw members is moveable with respect to the other from a spaced-apart position to an approximated position for grasping tissue therebetween. A knife is longitudinally translatable with respect to the first and second jaw members between a retracted position, an intermediate position, and an extended position. The knife is coupled to one (or both) of the jaw members via a pin-slot engagement such that, upon translation of the knife from the retracted position to the intermediate position, the first and second jaw members are moved to the approximated position to grasp tissue therebetween and such that, upon translation of the knife from the intermediate position to the extended position, the knife is extended between the jaw members to cut tissue grasped therebetween.

In one embodiment, each of the first and second jaw members includes an opposed electrically conductive tissue sealing surface adapted to connect to an electrosurgical energy source to communicate energy to tissue grasped between the jaw members.

In another embodiment, one (or both) of the first and second jaw members includes a knife channel defined therein. The knife channel(s) is configured to permit reciprocation of the knife therethrough. The knife channel(s) may define a T-shaped longitudinal cross-sectional configuration or an L-shaped longitudinal cross-sectional configuration. Further, the knife may define a longitudinal cross-sectional configuration complementary to longitudinal cross-sectional configuration of the knife channel(s).

In yet another embodiment, the knife includes a slot defined therein and wherein one of the jaw members, e.g., the first jaw member, includes a pin engaged within the slot. The slot defined within the knife is configured such that, when the knife is translated from the retracted position to the intermediate position, the first and second jaw members are moved from the spaced-apart position to the approximated position to grasp tissue therebetween. The slot may further be configured such that, upon translation of the knife from the intermediate position to the extended position, the knife is extended between the jaw members to cut tissue grasped therebetween.

Alternatively, the knife may include a pin engaged thereon in transverse relation relative thereto and the first and second jaw members may each include a slot defined therethrough. In such an embodiment, the slots are configured such that, when the knife is translated from the retracted position to the intermediate position, the first and second jaw members are moved from the spaced-apart position to the approximated position to grasp tissue therebetween. The slots may further be configured such that, upon translation of the knife from the intermediate position to the extended position, the knife is extended at least partially between the jaw members to cut tissue grasped therebetween.

In still another embodiment, when the first and second jaw members are disposed in the approximated position, a predetermined gap distance is defined therebetween.

In still yet another embodiment, a handle assembly is provided. The handle assembly is coupled to the end effector assembly and is selectively moveable between an initial position, a first actuated position, and a second actuated position for translating the knife between the retracted position, the intermediate position, and the extended position, respectively. The handle assembly may further include one or more feedback features for providing audible, tactile, and/or visual feedback as to the position of the handle assembly.

Another embodiment of a forceps provided in accordance with the present disclosure includes a handle assembly including a moveable handle moveable between a first position, a second position, and a third position. The handle assembly has a shaft extending distally therefrom. An end effector assembly is disposed at a distal end of the shaft and includes first and second jaw members disposed in opposed relation relative to one another. One or both of the jaw members is moveable with respect to the other from a spaced-apart position to an approximated position for grasping tissue therebetween. One or both of the jaw members further includes a pin extending therethrough. A knife bar is disposed within the shaft and is longitudinally translatable with respect to the first and second jaw members between a retracted position, an intermediate position, and an extended position upon movement of the moveable handle between the first position, the second position, and the third position, respectively. The knife bar includes a slot defined therein that is configured to receive the pin of the jaw member(s) therethrough such that, upon translation of the knife bar from the retracted position to the intermediate position, the first and second jaw members are moved to the approximated position to grasp tissue therebetween and such that, upon translation of the knife bar from the intermediate position to the extended position, the knife bar is extended between the jaw members to cut tissue grasped therebetween.

Yet another embodiment of a forceps provided in accordance with the present disclosure similarly includes a handle assembly having a moveable handle that is moveable between a first position, a second position, and a third position. A shaft extends distally from the handle assembly and includes an end effector assembly disposed at a distal end thereof. The end effector assembly includes first and second jaw members disposed in opposed relation relative to one another. One or both of the jaw members is moveable with respect to the other from a spaced-apart position to an approximated position for grasping tissue therebetween. One or both of the jaw members includes a proximal flange having a slot defined therethrough. A knife bar is disposed within the shaft and is longitudinally translatable with respect to the first and second jaw members between a retracted position, an intermediate position, and an extended position upon movement of the moveable handle between the first position, the second position, and the third position. The knife bar includes a pin engaged therein and extending transversely relative thereto that is configured for engagement within the slot(s) of the jaw member(s) such that, upon translation of the knife bar from the retracted position to the intermediate position, the first and second jaw members are moved to the approximated position to grasp tissue therebetween and such that, upon translation of the knife bar from the intermediate position to the extended position, the knife bar is extended between the jaw members to cut tissue grasped therebetween.

BRIEF DESCRIPTION OF THE DRAWINGS

Various embodiments of the subject instrument are described herein with reference to the drawings wherein.

DETAILED DESCRIPTION

Figure 1:
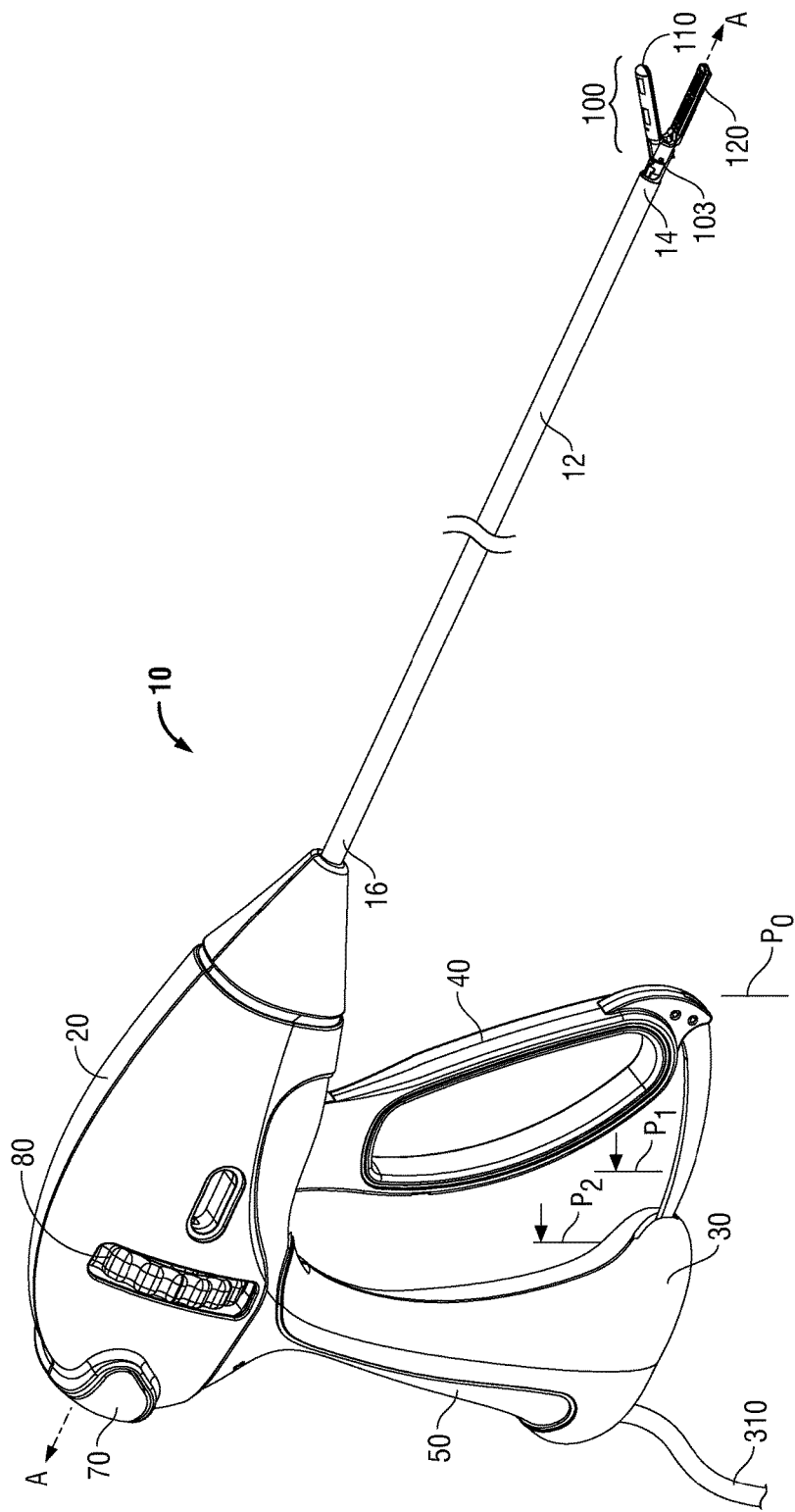
FIG. 1 is a perspective view of a forceps having an end effector assembly in accordance with an embodiment of the present disclosure.

Embodiments of the presently disclosed surgical instrument are described in detail with reference to the drawing figures wherein like reference numerals identify similar or identical elements. As used herein, the term "distal" refers to the portion that is being described that is further from a user, while the term "proximal" refers to the portion that is being described that is closer to a user.

Turning now to FIG. 1, a forceps 10 is shown including a housing 20, a handle assembly 30, an actuator 70, a rotating assembly 80, and an end effector assembly 100. Forceps 10 further includes a shaft 12 having a distal end 14 configured to mechanically engage end effector assembly 100 and a proximal end 16 that mechanically engages housing 20. Forceps 10 also includes electrosurgical cable 310 that connects forceps 10 to a generator (not shown) or other suitable power source, although forceps 10 may alternatively be configured as a battery-powered instrument. Cable 310 has sufficient length to extend through shaft 12 in order to provide electrical energy to at least one of jaw members 110 and 120 of end effector assembly 100. Rotating assembly 80 is rotatable in either direction about a longitudinal axis "A-A" to rotate end effector assembly 100 about longitudinal axis "A-A" with respect to shaft 12.

Figure 2:
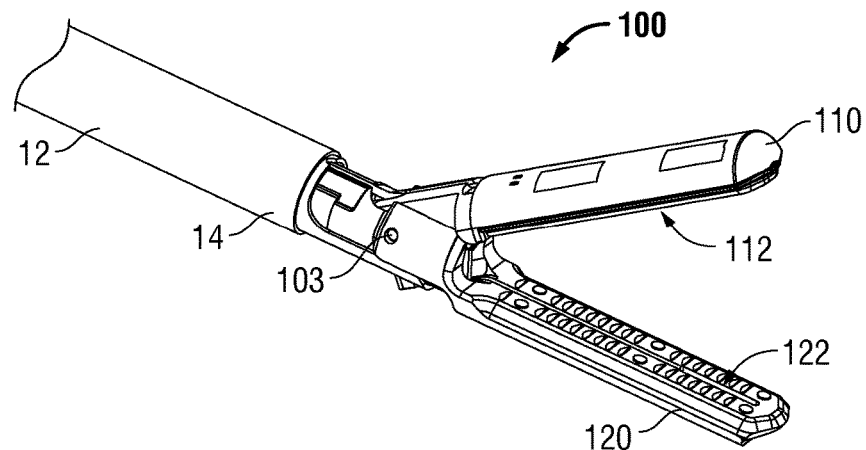
FIG. 2 is an enlarged, perspective view of the end effector assembly of FIG. 1.

Turning now to FIG. 2, end effector assembly 100 is shown attached at a distal end 14 of shaft 12. End effector assembly 100 includes a pair of opposing jaw members 110 and 120. End effector assembly 100 is designed as a unilateral assembly, i.e., jaw member 120 is fixed relative to the shaft 12 and jaw member 110 is moveable, e.g., pivotable, relative to jaw member 120 between a spaced-apart position and an approximated position. However, either, or both jaw members 110, 120 may be moveable with respect to the other between the spaced-apart and approximated positions.

With continued reference to FIG. 2, each jaw member 110, 120 includes an electrically conductive tissue sealing surface 112, 122, respectively, that is dimensioned to oppose the other. Accordingly, when jaw members 110, 120 are moved to the approximated position, tissue is grasped between sealing surfaces 112 122. With tissue grasped between sealing surfaces 112, 122, electrical energy may be supplied to one or both of jaw members 110, 120, such that the electrical energy is conducted between tissue sealing surfaces 112, 122 and through tissue grasped therebetween to effect a tissue seal. Actuator 70 (FIG. 1) may be selectively actuatable to supply electrical energy to jaw members 110, 120 or, alternatively, electrical energy may be automatically supplied to jaw members 110, 120, e.g., upon movement of jaw members 110, 120 to a position for grasping tissue.

Figure 5:
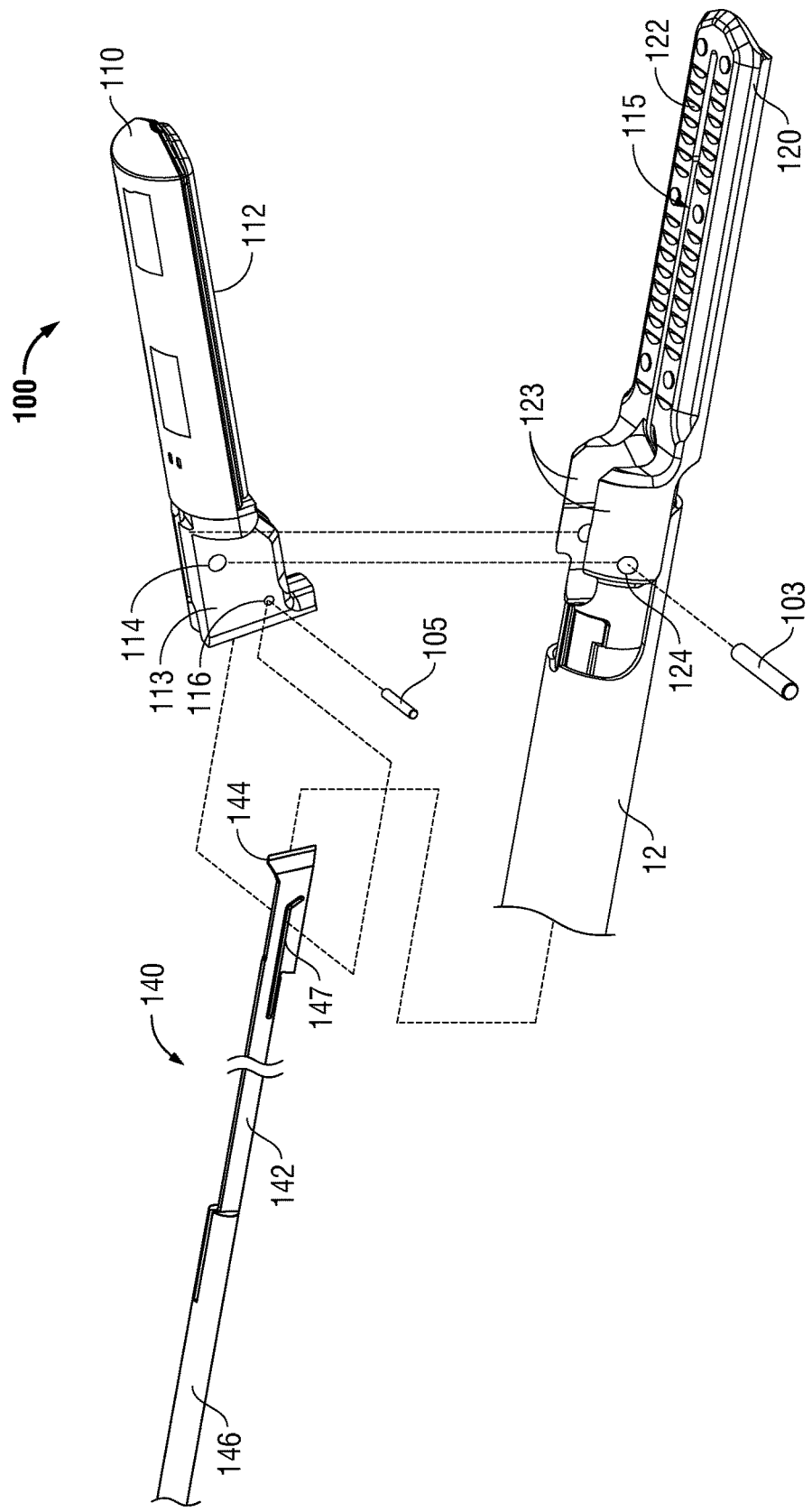
FIG. 5 is a perspective view of the end effector assembly of FIG. 1 shown with parts separated.

As best shown in FIG. 5, and as mentioned above, jaw members 110, 120 are pivotably coupled to one another via pivot pin 103. More particularly, jaw member 110 includes a pair of proximal flanges 113, each having a first aperture 114 defined therethrough. Similarly, jaw member 120 includes a pair of proximal flanges 123, each having a first aperture 124 defined therethrough. Proximal flanges 123 of jaw member 120 are further spaced than proximal flanges 113 of jaw member 110, such that, during assembly, proximal flanges 113 of jaw member 110 are inserted between proximal flanges 123 of jaw member 120 to align first apertures 114 of proximal flanges 113 of jaw member 110 and first apertures 124 of proximal flanges 123 of jaw member 120. Pivot pin 103 is disposed through and engaged within first apertures 114 and 124 of jaw members 110, 120, respectively, to securely engage jaw members 110, 120 to one another and to permit jaw members 110, 120 to pivot relative to one another between the spaced-apart position and the approximated position.

Figure 3:
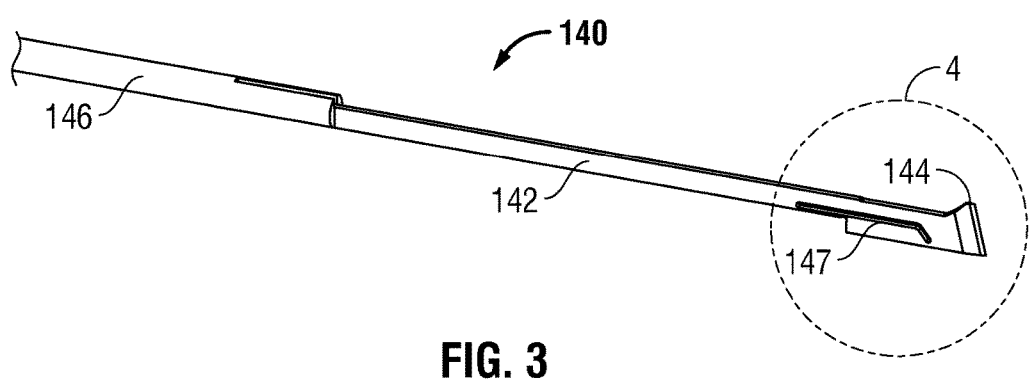
FIG. 3 is a perspective view of a knife assembly for use with the end effector assembly of FIG. 1.
Figure 4:
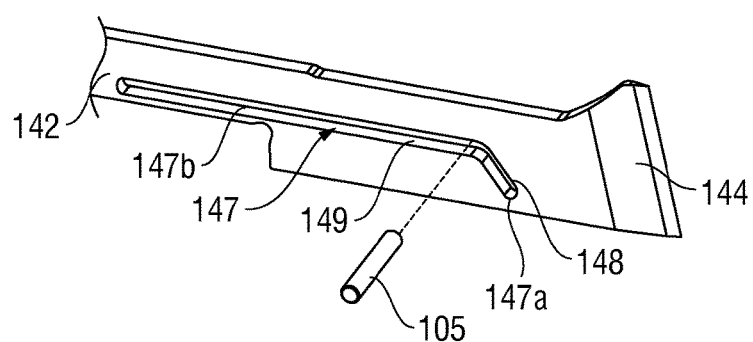
FIG. 4 is an enlarged, perspective view of the distal end of the knife assembly of FIG. 3.

Referring now to FIG. 5, in conjunction with FIGS. 3-4, a knife assembly 140 is disposed within shaft 12. As shown in FIG. 5, knife assembly 140 includes a knife bar 142 and a knife blade 144 disposed at a distal end of knife bar 142. Knife bar 142 is engaged to a knife holder 146 at a proximal end thereof, as shown in FIG. 3. As will be described in detail below, knife holder 146 extends proximally through shaft 12 into housing 20 (FIG. 1), ultimately coupling to moveable handle 40 (FIG. 1) to permit a user to selectively control the longitudinal translation of knife holder 146 and, thus, knife bar 142.

With continued reference to FIGS. 3-5, knife bar 142 extends distally from knife holder 146 and is coupled to jaw member 110 such that, when knife bar 142 is translated distally, e.g., upon actuation of moveable handle 40 (FIG. 1), jaw member 110 is pivoted about pivot pin 103 and moved with respect to jaw member 120 from the spaced-apart position to a position to grasp tissue therebetween. Upon further distal translation of knife bar 142, e.g., upon further actuation of moveable handle 40 (FIG. 1), knife blade 144 is advanced distally from shaft 12 through jaw members 110, 120 to cut tissue grasped therebetween. Accordingly, a knife channel 115 is defined within one or both jaw members 110, 120 to permit reciprocation of knife blade 144 therethrough.

As mentioned above, knife bar 142 is coupled to jaw member 110. More particularly, proximal flanges 113 of jaw member 110 each include a second aperture 116 defined therethrough and offset below first apertures 114, while knife bar 142 includes a longitudinal slot 147 defined therein. During assembly, knife bar 142 is positioned between proximal flanges 113 of jaw member 110 and a pin 105 is inserted through second aperture 116 of one proximal flange 113 of jaw member 110, through slot 147 of knife bar 142, and through second aperture 116 of the other proximal flange 113 of jaw member 110. Pin 105 is secured within second apertures 116 of proximal flanges 113 on either side of knife bar 142 to securely couple knife bar 142 and jaw member 110 to one another. Alternatively, as will be described below with reference to FIG. 13, a drive pin 250 may be transversely engaged within knife bar 242, with flanges 213, 227 of jaw members 210, 220, respectively, defining slots 216, 226 therethrough.

As a result of the above-described coupling of knife bar 142 and jaw member 110, pin 105 is translated along slot 147 of knife bar 142 when knife bar 142 is translated longitudinally with respect to jaw member 110 due to the engagement of pin 105 within second apertures 116 of proximal flanges 113 of jaw member 110. Further, as pin 105 is translated along slot 147, the transverse position of pin 105 relative to longitudinal axis "A-A" is determined by the configuration of slot 147 of knife bar 142. For example, if pin 105 were translated along an upwardly sloping portion of slot 147, slot 147 would urge pin 105 upwardly, e.g., in a positive direction relative to longitudinal axis "A-A." The upward urging of pin 105 would thereby urge jaw member 110 to rotate in a first direction about pivot pin 103 due to the offset position of pin 105 relative to pivot pin 103. On the other hand, if pin 105 were translated along a downwardly sloping portion of slot 147, pin 105 would be urged downwardly, e.g., in a negative direction relative to longitudinal axis "A-A," thereby urging jaw member 110 to rotate in a second, opposite direction about pivot pin 103. Put more generally, the configuration of slot 147 of knife bar 142 controls the displacement of pin 105 relative to longitudinal axis "A-A" as knife bar 142 is translated relative to jaw member 110. The displacement of pin 105, e.g., the upward or downward movement of pin 105, as knife bar 142 is translated relative to jaw member 110, in turn, urges jaw member 110 to rotate about pivot pin 103 in a first or second direction, e.g., in a clockwise or counterclockwise direction, depending on the direction of displacement.

Accordingly, slot 147 of knife bar 142 may be specifically configured to pivot jaw member 110 about pivot pin 103 and relative to jaw member 120 from the spaced-apart position to the approximated position, from the approximated position to the spaced-apart position, or to maintain the relative position of jaw members 110, 120, as knife bar 142 is translated relative to jaw members 110, 120. Further, slot 147 may define segments of varying configuration such that jaw members 110, 120 may be approximated (in a grasped position), maintained in position, and/or opened upon translation of knife bar 142 relative to jaw members 110, 120 in a single direction. As such, although only one particular configuration of slot 147 will be described below, slot 147 may be configured to achieve any desired combination of approximating, opening and maintaining the position of jaw members 110, 120 upon translation of knife bar 142 with respect to jaw members 110, 120.

Figure 6A:
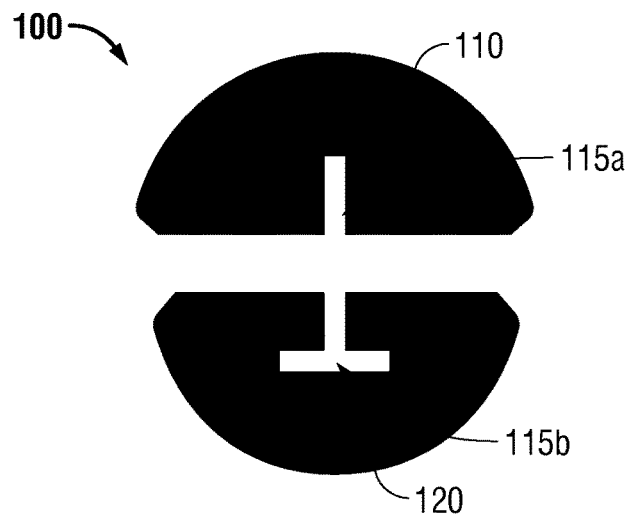
FIG. 6A is a transverse, cross-sectional view of the end effector assembly of FIG. 1.
Figure 6B:
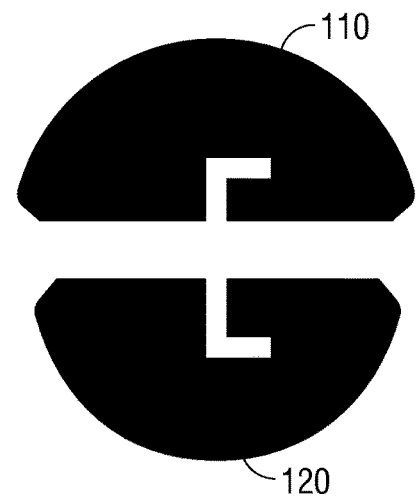
FIG. 6B is a transverse, cross-sectional view of another embodiment of an end effector assembly similar to the end effector assembly of FIG. 1.
Figure 6C:
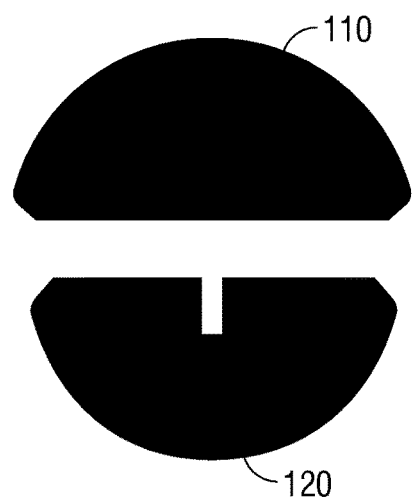
FIG. 6C is a transverse, cross-sectional view of yet another embodiment of an end effector assembly similar to the end effector assembly of FIG. 1.

Turning now to FIGS. 6A-6C, end effector assembly 100 is shown with jaw members 110, 120 disposed in the approximated or grasped position. As shown in FIG. 6A, jaw member 120 includes a "T"-shaped blade channel 115b. "T"-shaped blade channel 115b, in conjunction with blade channel 115a of jaw member 110, is configured to permit reciprocation of a corresponding "T"-shaped blade (not shown) therethrough. Although not shown, jaw member 110 may similarly include a "T"-shaped blade channel such that blade channels 115a, 115b of jaw members 110, 120, respectively, cooperate to permit reciprocation of an "I"-shaped blade (not shown) therethrough. Alternatively, as shown in FIG. 6B, jaw member 110 and/or jaw member 120 may include an "L"-shaped blade channel for reciprocation of a correspondingly shaped blade (not shown) therethrough or, as shown in FIG. 6C, only one jaw member, e.g., jaw member 120, may include a blade channel 115b defined therein. Put more generally, blade channels 115a, 115b of jaw members 110, 120, respectively, may be configured in any suitable fashion such that knife blade 144 is permitted to translate therethrough, although jaw member 110 and/or jaw member 120 need not include a blade channel defined therein.

Figure 7:
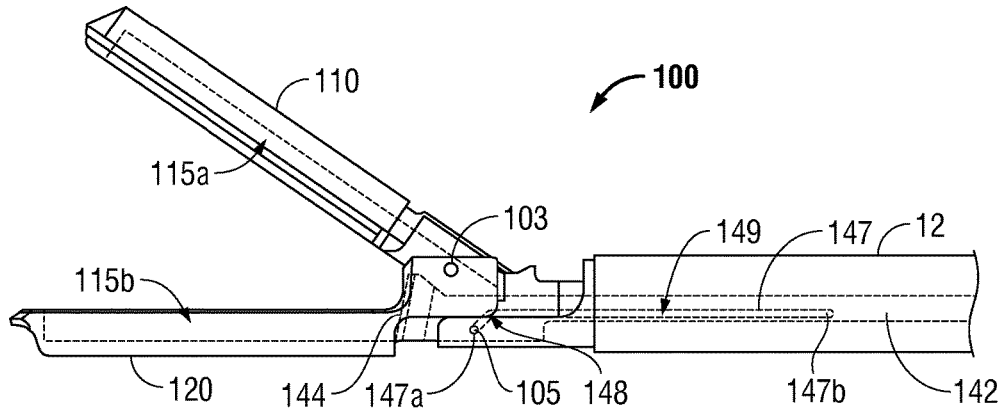
FIG. 7 is a side, cross-sectional view of the end effector assembly of FIG. 1 with the knife assembly in a first position.
Figure 8:
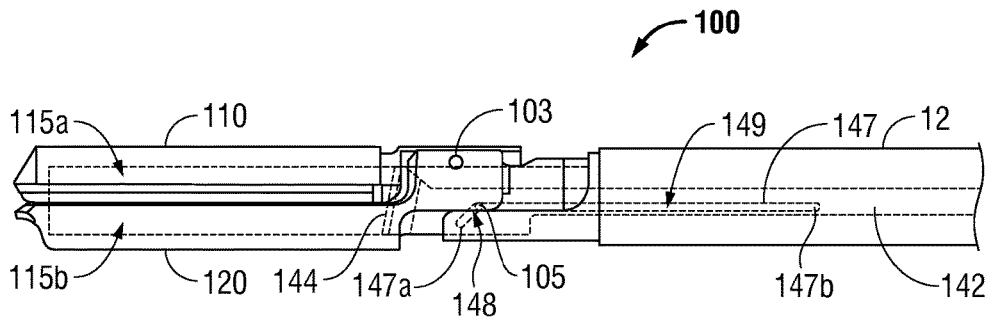
FIG. 8 is a side, cross-sectional view of the end effector assembly of FIG. 1 with the knife assembly in a second position.
Figure 9:
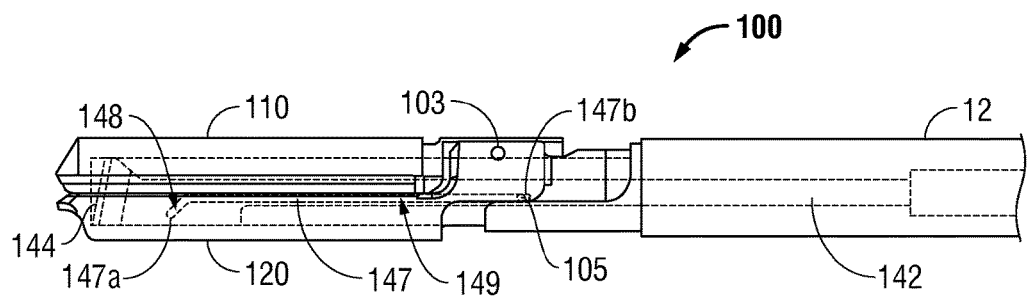
FIG. 9 is a side, cross-sectional view of the end effector assembly of FIG. 1 with the knife assembly in a third position.

Turning now to FIGS. 7-9, the use an operation of end effector assembly 100 is described. Initially, as shown in FIG. 7, knife bar 142 is disposed in a proximal-most position such that pin 105 is disposed at a distal end 147a of slot 147 (see FIG. 4). As shown in FIG. 7, this position corresponds to the spaced-apart position of jaw members 110, 120. Further, in this proximal-most position, knife blade 144 is disposed between flanges 113, 123 of jaw members 110, 120, respectively, and does not extend between jaw members 110, 120. Accordingly, knife blade 144 is not exposed when jaw members 110, 120 are in the spaced-apart position. In fact, as will become more apparent below, blade 144 is inhibited from extending between jaw members 110, 120 when jaw members 110, 120 are disposed in the spaced-apart position due to the configuration of slot 147 defined within knife bar 142. In use, with jaw members 110, 120 in the spaced-apart position, end effector assembly 100 is positioned such that tissue to be sealed and/or divided is positioned between jaw members 110, 120. Moreover, slot 147 may be sized to predetermine the relative distance that jaw members 110, 120 may open, e.g., slot 147 may act as an open stop or limiter for forceps 10.

Next, as shown in FIG. 8, knife bar 142 is translated distally from the proximal-most position to an intermediate position. More particularly, as knife bar 142 is translated distally, pin 105 is translated along ramped portion 148 of slot 147. As pin 105 is translated along ramped portion 148 of slot 147, pin 105 is urged upwardly, thereby urging jaw member 110 to rotate about pivot pin 103 and with respect to jaw member 120 to the approximated, or grasped position. Knife bar 142 and/or pin 105 may include a locking feature (not shown), e.g., a mating recess/protrusion, or other suitable locking feature for releasably fixing knife bar 142 in this intermediate position. Further, handle assembly 30 (FIG. 1) may include one or more locking features (not shown) to releasably fix knife bar 142 in the proximal-most position or the intermediate position.

With continued reference to FIG. 8, as can be appreciated, the length and slope of ramped portion 148 of slot 147 determines the transverse displacement of pin 105 with respect to longitudinal axis "A-A," that, in turn, determines the degree of rotation of jaw member 110 about pivot pin 103. Accordingly, slot 147 may be configured to achieve a desired gap distance "g" between sealing surfaces 112, 122 of jaw members 110, 120, respectively, when moved to the approximated position, e.g., about 0.001 inches to about 0.006 inches. For example, where ramped portion 148 of slot 147 defines a more gradual slope, or where ramped portion 148 of slot 147 defines a relatively short length, pin 105 is only displaced a relatively small distance with respect to longitudinal axis "A-A" upon translation along ramped portion 148 of slot 147. As such, jaw member 110 is rotated a relatively small degree about pivot pin 103, resulting in a relatively large gap distance "g" between sealing surfaces 112, 122 of jaw members 110, 120, respectively, in the approximated position. On the other hand, where ramped portion 148 of slot 147 defines a steeper slope, or a larger length, pin 105 is displaced a relatively large distance with respect to longitudinal axis "A-A" upon translation along ramped portion 148 of slot 147 such that jaw member 110 is rotated a greater degree with respect to pivot pin 103 to the approximated position to define a relatively small gap distance between sealing surfaces 112, 122 of jaw members 110, 120, respectively. Further, ramped portion 148 of slot 147 of knife bar 142 may include several incremental intermediate positions, e.g., ramped portion 148 may define a stepped, rather than a continuously-sloped configuration, corresponding to different gap distances "g" such that the gap distance between sealing surfaces 112, 122 of jaw members 110, 120, respectively, may be varied, e.g., depending on diameter and/or composition of tissue to be grasped and sealed, upon movement of jaw members 110, 120 to the approximated position.

In the intermediate position, as shown in FIG. 8, knife bar 142 has been translated distally from the proximal-most position. However, knife blade 144 remains disposed between flanges 113, 123 of jaw members 110, 120, respectively, and does not extend between jaw members 110, 120. Accordingly, knife bar 142 may be translated from the proximal-most position to the intermediate position to move jaw members 110, 120 from the spaced-apart position to the approximated position to grasp tissue therebetween without exposing blade 144 to tissue. In other words, the grasping of tissue, e.g., via approximation of jaw members 110, 120, is independent of the cutting of tissue, e.g., via advancement of knife blade 144 between jaw members 110, 120.

In use, with tissue grasped between jaw members 110, 120 and, more particularly, between sealing surfaces 112, 122 of jaw members 110, 120, respectively, electrosurgical energy may be supplied to sealing surfaces 112, 122 and conducted through tissue grasped therebetween to effect a tissue seal.

Turning now to FIG. 9, once tissue has been sealed, or where it is desired to simply grasp and divide tissue, knife bar 142 is advanced from the intermediate position to an extended position. As mentioned above, pivot pin 103 is offset above pin 105 such that knife bar 142 may pass under pivot pin 103 upon translation from the intermediate position to the extended position. In the extended position, as shown in FIG. 9, knife bar 142 is advanced between jaw members 110, 120 such that knife blade 144 dissects tissue grasped therebetween. More particularly, knife bar 142 is translated through knife channel 115a and/or knife channel 115b defined within jaw members 110, 120, respectively. As knife bar 142 is translated to the extended position, pin 105 is translated along slot 147 to a proximal end 147b thereof. Slot 147 of knife bar 142 defines a longitudinal portion 149 centered on longitudinal axis "A-A" and extending proximally from ramped portion 148 such that, as knife bar 142 is translated distally from the intermediate position to the extended position, pin 105 is maintained on longitudinal axis "A-A" and, thus, jaw members 110, 120 are maintained in the approximated position.

Once tissue has been grasped, sealed and/or divided, as mentioned above, knife bar 142 may be translated proximally from the extended position, through the intermediate position, and back to the proximal-most position to move jaw members 110, 120 back to the spaced-apart position to release the sealed and divided tissue. Thereafter, end effector assembly 100 may be removed from the surgical site.

Figure 10:
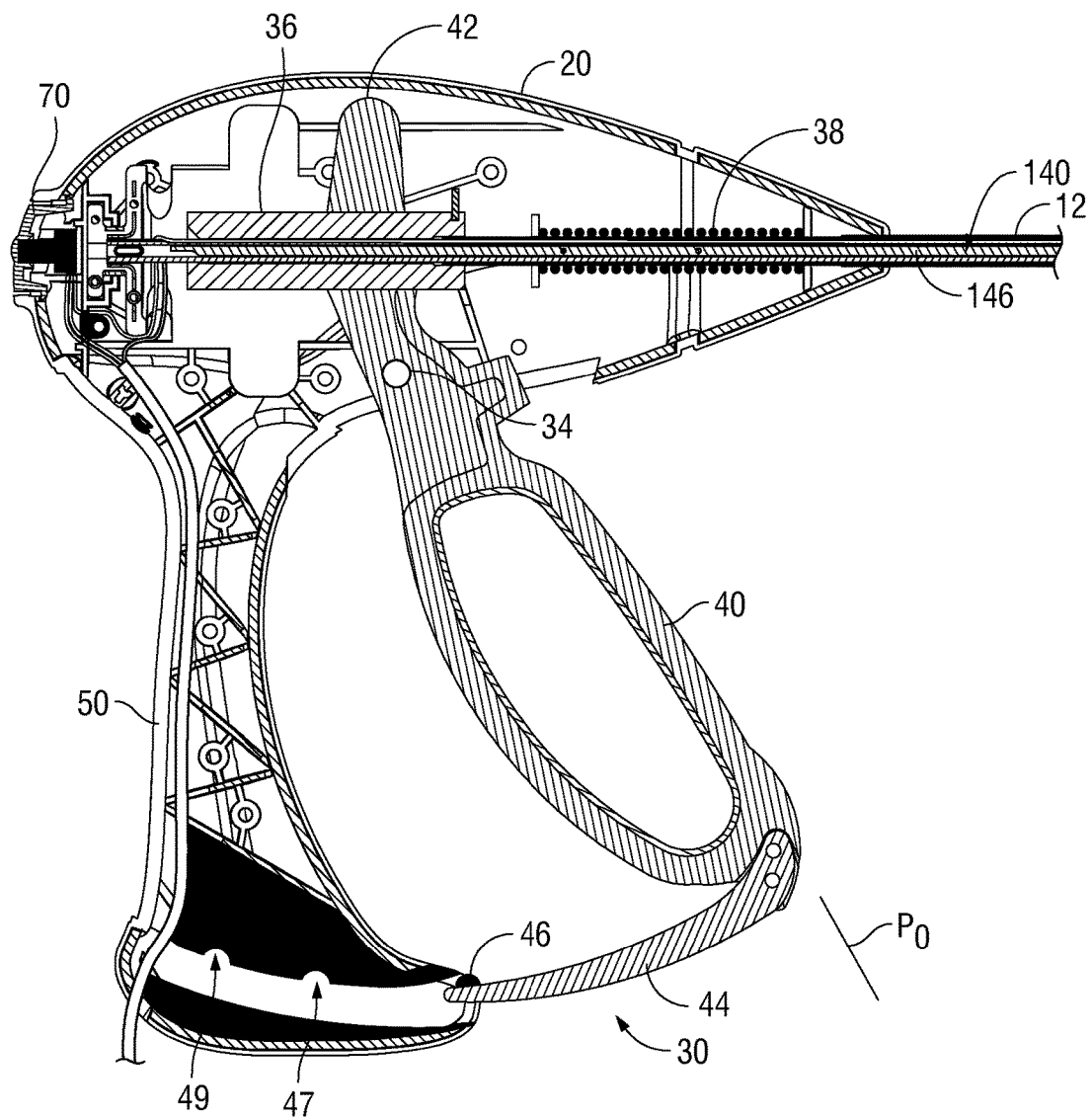
FIG. 10 is a side view of the forceps of FIG. 1 wherein a portion of the housing has been removed to show the internal components therein and wherein the handle is disposed in a first position.
Figure 11:
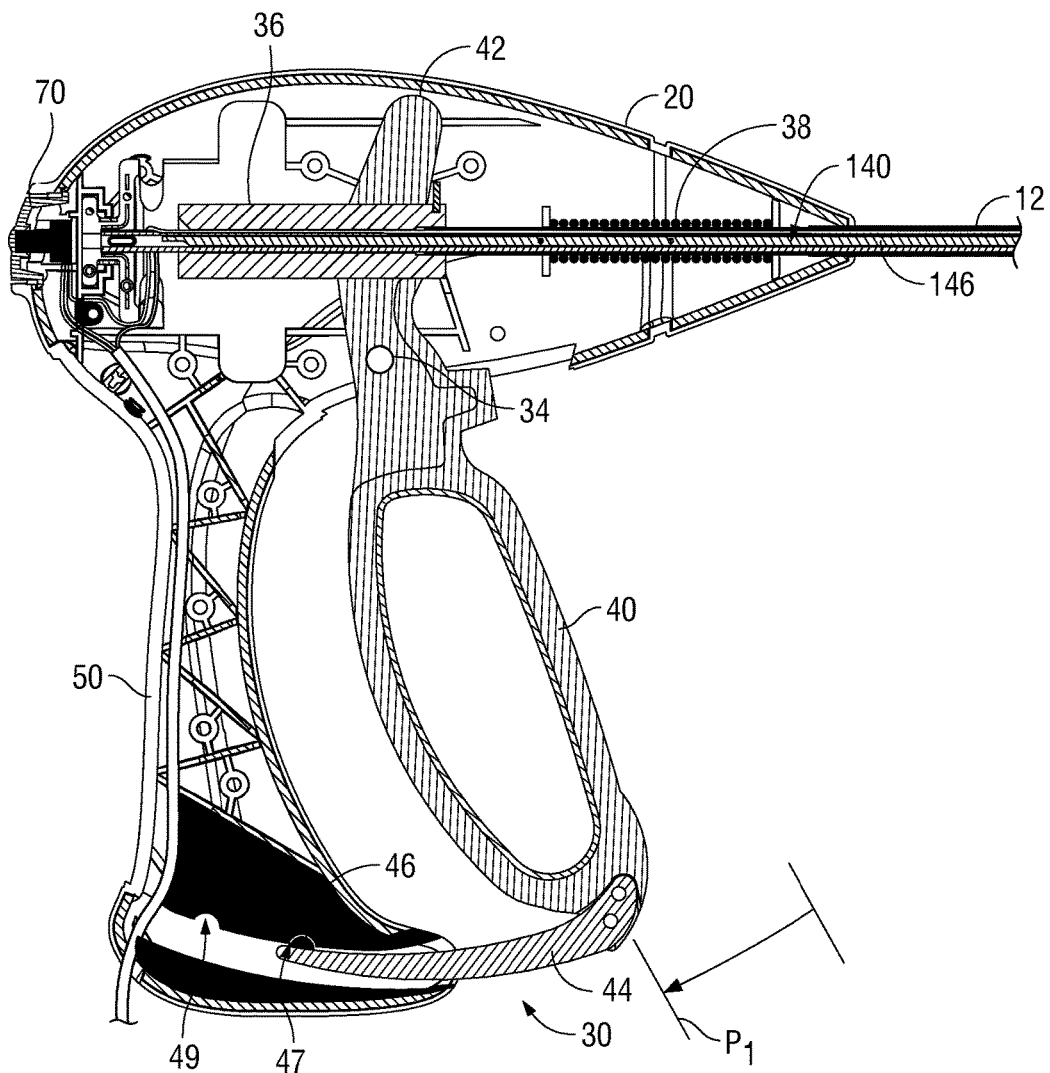
FIG. 11 is a side view of the forceps of FIG. 1 wherein a portion of the housing has been removed to show the internal components therein and wherein the handle is disposed in a second position.
Figure 12:
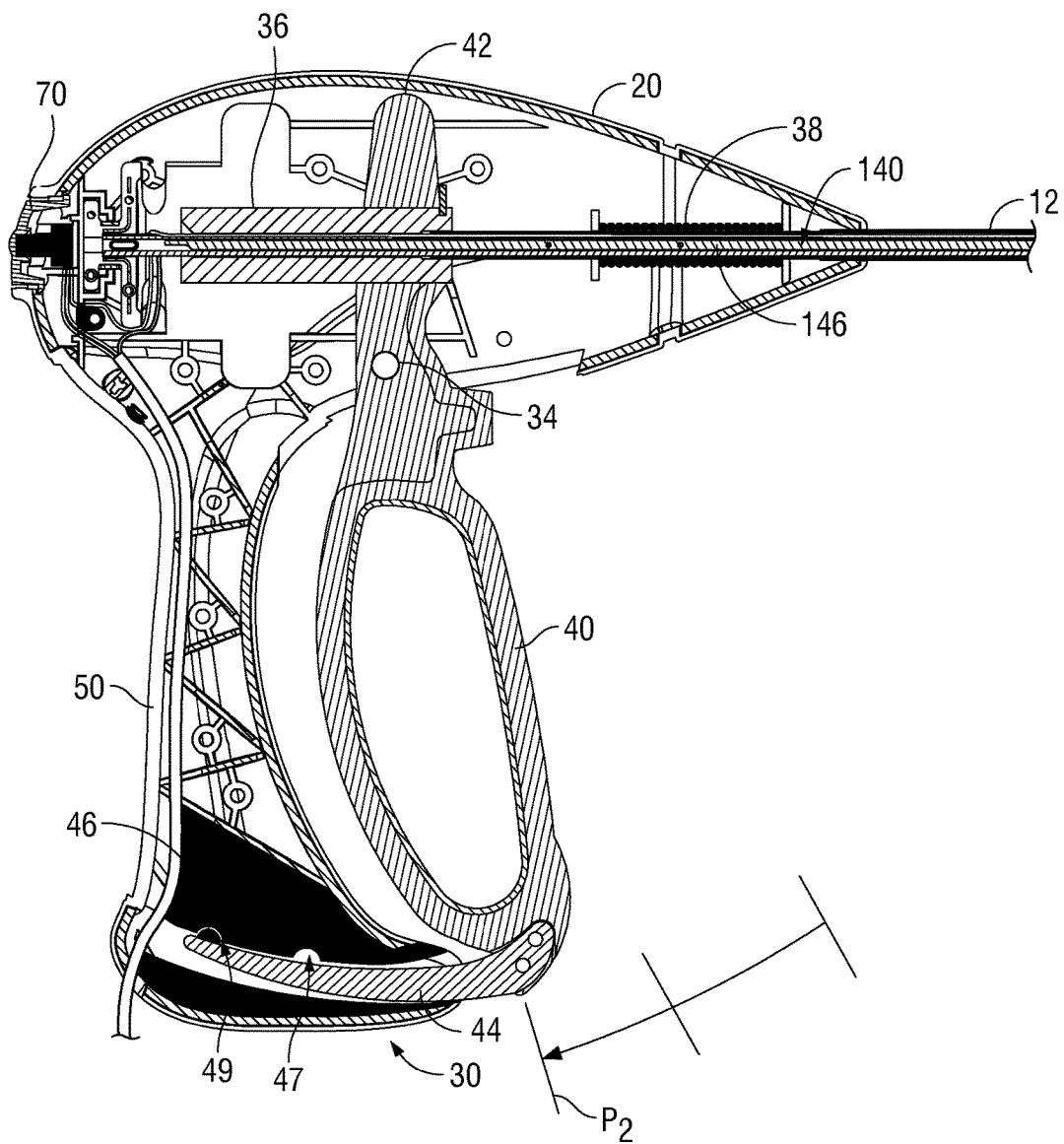
FIG. 12 is a side view of the forceps of FIG. 1 wherein a portion of the housing has been removed to show the internal components therein and wherein the handle is disposed in a third position.
Figure 13:
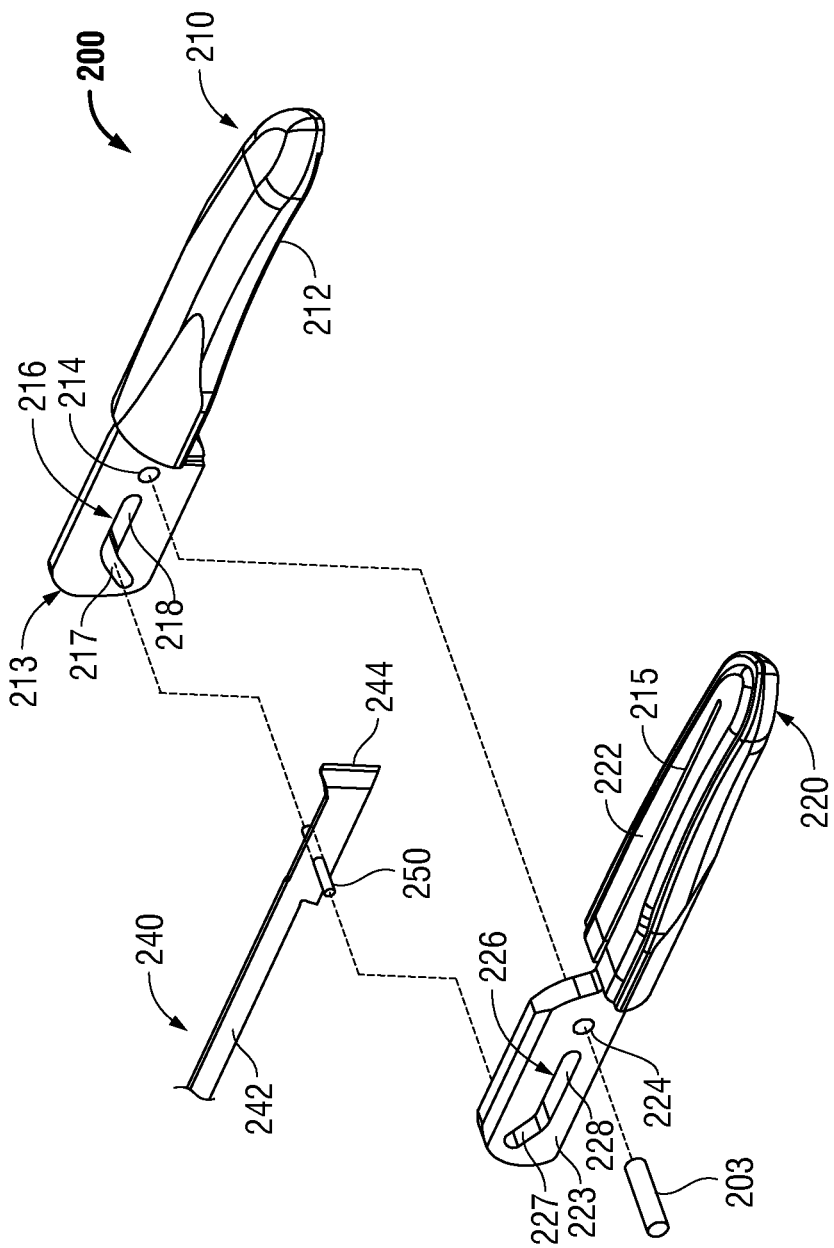
FIG. 13 is a perspective view of another embodiment of an end effector assembly provided in accordance with the present disclosure and shown with parts separated.

Referring now to FIGS. 10-12, in conjunction with FIG. 1, handle assembly 30, configured to selectively translate knife bar 142 between the proximal-most position, the intermediate position, and the extended position, will be described. Handle assembly 30 includes a fixed handle 50 and a moveable handle 40. Fixed handle 50 is integrally associated with housing 20 and moveable handle 40 is moveable relative to fixed handle 50. Moveable handle 40 includes a pair of flanges 42 that extend into housing 20 on either side of knife holder 146. Flanges 42 and, thus, moveable handle 40 are pivotably coupled to housing 20 via pivot pin 34. Flanges 42 abut knife sleeve 36 that is fixedly engaged to knife holder 146, as best shown in FIGS. 12-14. Further, a spring 38, or other biasing member, may be disposed about knife holder 146 within housing 20 to bias knife assembly 140 toward the proximal-most position, thereby biasing moveable handle 40 toward the initial position "$P_0$."

With continued reference to FIGS. 1 and 10-12, moveable handle 40 is moveable with respect to fixed handle 50 between an initial position "$P_0$" (FIGS. 1 and 10), a first actuated position "$P_1$" (FIG. 11), and a second actuated position "$P_2$" (FIG. 12). Due to the abutting relationship between flanges 42 of moveable handle 40 and knife sleeve 36, moving handle 40 between the initial position "$P_0$," first actuated position "$P_1$," and second actuated position "$P_2$," translates knife holder 146 and, thus, knife blade 142 between the proximal-most position (FIG. 7), the intermediate position (FIG. 8), and the extended position (FIG. 9), respectively. As will be described below, handle assembly 30 may include one or more feedback features e.g., latch member 44 of moveable handle 40, for providing audible, tactile, visual, or other feedback to the user as to the position of moveable handle 40 with respect to fixed handle 50. Further, handle assembly 40 may include a locking mechanism (not shown) for releasably retaining moveable handle 40 in the first actuated position "$P_1$" and/or the second actuated position "$P_2$."

In the initial position "$P_0$," jaw members 110, 120 are disposed in the spaced-apart position, as shown in FIG. 1. When moveable handle 40 is moved from the initial position to the first actuated position "$P_1$," knife bar 142 is advanced distally such that jaw members 110, 120 are moved to the approximated position to grasp tissue therebetween (see FIG. 8). Upon further actuation of moveable handle 40, e.g., upon movement of moveable handle 40 from the first actuated position "$P_1$" to the second actuated position "$P_2$," knife 142 is advanced further distally to extend between jaw members 110, 120 to cut tissue grasped therebetween.

More specifically, as shown in FIG. 10, when moveable handle 40 is disposed in the initial position "$P_0$," knife assembly 140 is disposed in the proximal-most position and, thus, jaw members 110, 120 are disposed in the spaced-apart position (see FIG. 7). Moveable handle 40, knife assembly 140 and jaw members 110, 120 are maintained in their respective positions under the bias of spring 38. Further, with moveable handle 40 disposed in the initial position "$P_0$," latch member 44, that is securely engaged thereto, extends minimally into fixed handle 50.

As shown in FIG. 11, as moveable handle 40 is moved from the initial position "$P_0$," to the first actuated position "$P_1$," against the bias of spring 38, knife assembly 140 is advanced distally to the intermediate position (see FIG. 8), jaw member 110, 120 are moved to the approximated position (see FIG. 8) to grasp tissue therebetween, and latch member 44 is advanced further into fixed handle 50 such that protrusion 46 of latch member 44 engages first recess 47 defined within fixed handle 50. The engagement of protrusion 46 and first recess 47 may provide an audible "click," alerting the user that moveable handle 40 is disposed in the first actuated position "$P_1$" and, thus, that jaw members 110, 120 are disposed in the approximated position. A locking mechanism (not shown) may also be provided to fix moveable handle in the first actuated position "$P_1$." With jaw members 110, 120 disposed in the approximated position (FIG. 8) and grasping tissue therebetween, actuator 70 may be depressed to supply electrosurgical energy to sealing surfaces 112, 122 of jaw members 110, 120, respectively, to effect a tissue seal.

Once tissue has been adequately sealed, or where it is desired to only cut tissue, moveable handle 40 may be moved further against the bias of spring 38 from the first actuated position "$P_1$" to the second actuated position "$P_2$." As mentioned above, moving moveable handle 40 to the second actuated position "$P_2$" advances knife blade 144 between jaw members 110, 120, e.g., through blade channels 115a, 115b (FIG. 6A), to cut tissue disposed therebetween. As moveable handle 40 is moved from the first actuated position "$P_1$" to the second actuated position "$P_2$," latch member 44 is advanced further into fixed handle 50 such that protrusion 46 of latch member 44 engages second recess 49 defined within fixed handle 50. The engagement of protrusion 46 and second recess 49 may provide an audible "click," alerting the user that moveable handle 40 is disposed in the second actuated position "$P_2$" and, thus, that knife blade 144 is extended through blade channels 115a, 115b of jaw members 110, 120, respectively. Thereafter, moveable handle 40 may be released, or otherwise returned to the initial position "$P_0$," allowing knife assembly 140 to return to the proximal-most position and, thus, allowing jaw members 110, 120 to return to the spaced-apart position.

Handle assembly 30 may be configured as a two-step mechanism, e.g., moveable handle 40 may be configured to first move from the initial position "$P_0$" to the first actuated position "$P_1$" and then, upon the application of additional force, move from the first actuated position "$P_1$" to the second actuated position "$P_2$", or, alternatively, may be configured as a continuous, single stroke mechanism, e.g., moveable handle 40 is moved from the initial position "$F_0$" through the first actuated position "$P_1$" for grasping and or sealing tissue and to the second actuated position "$P_2$" for cutting tissue. Other configurations of handle assembly 30 are also contemplated, so long as handle assembly 30 is configured to move jaw member 110, 120 between the spaced-apart position and the approximated position, and to advance knife blade 144 therebetween.

As can be appreciated from the above, handle assembly 30 and knife assembly 140 cooperate with end effector assembly 100 to move jaw members 110, 120 between the spaced-apart and approximated positions and to advance knife blade 144 therebetween with minimal components. However, while the same mechanism is used to move jaw members 110, 120 between the spaced-apart and approximated positions to grasp (and seal) tissue and to advance knife blade 144 between jaw members 110, 120 to cut tissue, the grasping/sealing and cutting functions remain independent of one another. In other words, end effector assembly 100 may be used for grasping and sealing tissue, for grasping and cutting tissue, or for grasping, sealing, and cutting tissue.

Referring now to FIG. 13, another embodiment of an end effector assembly configured for use with forceps 10 (FIG. 1) provided in accordance with the present disclosure is shown generally identified by reference numeral 200. Similar to end effector assembly 100 (FIGS. 1-12), end effector assembly 200 includes a pair of opposing jaw members 210 and 220 each having an electrically conductive tissue sealing surface 212, 222 disposed on an opposed surface thereof. Jaw members 210, 220 are movable relative to one another from a spaced-apart position to an approximated position for grasping and sealing tissue disposed therebetween. End effector assembly 200 is designed as a bilateral assembly, i.e., both jaw members 210 and 220 are movable relative to one another, although end effector assembly 200 may alternatively be configured as a unilateral assembly, i.e., wherein one of jaw members 210, 220 is fixed in position.

With continued reference to FIG. 13, jaw members 210, 220 are pivotably coupled to one another via pivot pin 203. More particularly, each jaw member includes a proximal flange 213, 223, each of which defines an aperture 214, 224 therethrough that is configured to receive pivot pin 203 therethrough. Flanges 213, 223 of jaw members 210, 220, respectively, each further include a slot 216, 226 defined therethrough. Each slot 216, 226 includes an angled portion 217, 227, respectively, and a longitudinal portion 218, 228 that is substantially aligned with respective apertures 213, 223 relative to the longitudinal axis of end effector assembly 200.

A knife assembly 240, similar to knife assembly 140 (FIG. 5), is configured for positioning within shaft 12 (FIG. 1) and includes a knife bar 242 and a knife blade 244 disposed at a distal end of knife bar 242. Knife bar 242 includes a drive pin 250 disposed therethrough in transverse relation relative to knife bar 242. Drive pin 250 is engaged within each of slots 216, 226 of jaws 210, 220, respectively, such that, when knife bar 242 is translated distally, e.g., upon actuation of moveable handle 40 (FIG. 1), jaw members 210, 220 are pivoted about pivot pin 203 and relative to one another from the spaced-apart position to an approximated position to grasp tissue therebetween. More specifically, drive pin 250 is translated through angled portions 217, 227 of slots 216, 226, respectively, such that jaw members 210, 220 are brought into approximation with one another.

Upon further distal translation of knife bar 242, e.g., upon further actuation of moveable handle 40 (FIG. 1), knife blade 244 is advanced distally through knife channel(s) 215 of jaw member 210 and/or jaw member 220 to cut tissue grasped therebetween. More specifically, drive pin 250 is translated through longitudinal portions 218, 228 of slots 216, 226 to translate knife blade 244 longitudinally relative to jaw members 210, 220, respectively. As can be appreciated, proximal translation of knife bar 242, e.g., upon release, or return of moveable handle 40 (FIG. 1), returns knife blade 244 proximally and, ultimately, returns jaw members 210, 220 to the spaced-apart position.

The use, operation, and additional features of end effector assembly 100 described above with reference to FIGS. 1-12 apply similarly to end effector assembly 200 and, thus, will not be repeated here for purposes of brevity.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A forceps, comprising:
    first and second jaw members disposed in opposed relation relative to one another, at least one of the first and second jaw members moveable with respect to the other from a spaced-apart position to an approximated position for grasping tissue therebetween; and
    a knife bar movable with respect to the first and second jaw members between a retracted position, an intermediate position, and an extended position, the knife bar coupled to at least one of the first and second jaw members via a pin and slot engagement, the slot defining a ramped portion and a longitudinal portion, wherein movement of the knife bar from the retracted position to the intermediate position moves the pin along the ramped portion of the slot to move the first and second jaw members from the spaced-apart position to the approximated position to grasp tissue therebetween and wherein movement of the knife bar from the intermediate position to the extended position moves the pin along the longitudinal portion of the slot to extend the knife bar at least partially between the first and second jaw members to cut tissue grasped therebetween.

2. The forceps according to claim 1, wherein the knife bar includes the pin engaged therewith and extending transversely relative thereto, and wherein at least one of the first and second jaw members defines the slot therein.

3. The forceps according to claim 1, wherein at least one of the first and second jaw members includes the pin engaged therewith and extending transversely relative thereto, and wherein the knife bar defines the slot therein.

4. The forceps according to claim 1, wherein each of the first and second jaw members includes an opposed electrically conductive surface adapted to connect to an electrosurgical energy source to communicate energy to tissue grasped between the jaw members.

5. The forceps according to claim 1, wherein at least one of the first and second jaw members includes a knife channel defined therein, the at least one knife channel configured to permit reciprocation of the knife bar therethrough upon movement of the knife bar from the intermediate position to the extended position.

\* \* \* \* \*